(12) United States Patent
Looft

(10) Patent No.: US 8,648,028 B2
(45) Date of Patent: Feb. 11, 2014

(54) CAPSULE WITH ORGANIC/INORGANIC HYBRID WALL

(75) Inventor: Jan Looft, Niederbachem (DE)

(73) Assignee: Symrise AG, Holzminden (DE)

( * ) Notice: Subject to any disclaimer, the term of this patent is extended or adjusted under 35 U.S.C. 154(b) by 198 days.

(21) Appl. No.: 12/995,615

(22) PCT Filed: Jun. 2, 2009

(86) PCT No.: PCT/EP2009/056705
§ 371 (c)(1),
(2), (4) Date: Jan. 19, 2011

(87) PCT Pub. No.: WO2009/147119
PCT Pub. Date: Dec. 10, 2009

(65) Prior Publication Data
US 2011/0118161 A1    May 19, 2011

(30) Foreign Application Priority Data

Jun. 2, 2008 (DE) .......................... 10 2008 002 145

(51) Int. Cl.
| | | |
|---|---|---|
| C11D 17/00 | (2006.01) | |
| C11D 3/50 | (2006.01) | |
| C11D 3/37 | (2006.01) | |
| C11D 11/00 | (2006.01) | |
| A61K 8/02 | (2006.01) | |
| A61K 9/48 | (2006.01) | |
| A61K 9/50 | (2006.01) | |

(52) U.S. Cl.
USPC ............ 510/438; 510/101; 510/119; 510/276; 510/349; 510/400; 510/441; 510/466; 510/475; 510/515; 510/516; 424/401; 424/451; 424/497; 512/4

(58) Field of Classification Search
USPC ......... 510/466, 276, 438, 515, 516, 101, 119, 510/349, 400, 441, 475; 424/401, 451, 497; 512/4
See application file for complete search history.

(56) References Cited

U.S. PATENT DOCUMENTS

| | | | |
|---|---|---|---|
| 5,643,581 A * | 7/1997 | Mougin et al. ................. | 424/401 |
| 6,337,089 B1 * | 1/2002 | Yoshioka et al. .............. | 424/451 |
| 6,379,751 B1 * | 4/2002 | Schafer et al. ................. | 427/389 |
| 2003/0165692 A1 | 9/2003 | Koch et al. | |
| 2004/0182711 A1 | 9/2004 | Liang et al. | |
| 2005/0009720 A1* | 1/2005 | Delplancke et al. ........... | 510/336 |
| 2006/0036055 A1* | 2/2006 | Schafer et al. .................. | 528/44 |
| 2007/0042182 A1 | 2/2007 | Markus et al. | |
| 2007/0208152 A1* | 9/2007 | Hupfield ........................ | 526/245 |
| 2010/0267601 A1* | 10/2010 | Panandiker et al. .......... | 510/276 |
| 2011/0182844 A1* | 7/2011 | Wagner et al. ........... | 424/70.122 |

FOREIGN PATENT DOCUMENTS

| | | |
|---|---|---|
| WO | WO-0216020 A1 | 2/2002 |
| WO | WO-2009021989 A1 | 2/2009 |

OTHER PUBLICATIONS

International Search Report, Application No. PCT/EP2009/056705, filed Jun. 2, 2009.
European Office Action, European Application No. 09757500.5, dated May 2, 2012.

* cited by examiner

*Primary Examiner* — Lorna M Douyon
(74) *Attorney, Agent, or Firm* — Novak Druce Connolly Bove + Quigg LLP

(57) ABSTRACT

The present disclosure relates to a capsule having a core and a shell surrounding the core. The shell comprises a polymeric material produced by reacting a component (A) with a component (B). Component (A) comprises a polysiloxane bearing one or more amino groups and component (B) comprises one or more polyisocyanates. The disclosure also relates to processes for producing the capsules, methods of using the capsules, and to products containing the capsules.

19 Claims, 1 Drawing Sheet

CAPSULE WITH ORGANIC/INORGANIC HYBRID WALL

CROSS-REFERENCE TO RELATED APPLICATIONS

This application is a National Phase filing under 35 U.S.C. §371 of PCT/EP2009/056705, filed Jun. 2, 2009, which claims priority to DE Application No. 10 2008 002 145.8, filed in Germany on Jun. 2, 2008, the entire contents of which is incorporated herein by reference.

The present invention relates to specific capsules with a shell consisting of or comprising a material which can be produced by reacting amino group-bearing polysiloxanes with polyisocyanates, to processes for the production thereof, to uses of the capsules and to products comprising these capsules.

Nowadays, a large number of consumer goods are perfumed with odorous substances, in particular odorous substance compositions. However, in many cases, these are not optimally compatible with the consumer goods. This can lead to interactions with other ingredients, which interactions can impair and, in the worst case, destroy the odorous substances or the ingredients or both. Highly volatile odorous substances can also disappear from the perfumed product too rapidly, as a result of which the desired odor of the product changes or fades away prematurely.

A person skilled in the art is aware that it is possible to use, in order to overcome these problems, microcapsules (capsules having preferably a diameter in the micrometer range) which firstly enclose the odorous substances.

In other cases, the primary aim is not to perfume the sale product (consumer good) itself. Instead, another article is to be provided with a pleasant odor indirectly via the use of the product. A typical example of this is fabric softeners. In this case, it is not so much the odor of the fabric softener itself that is the target of the perfuming; instead, the aim is to perfume the laundry in the washing process as a result of the action of the fabric softener. In order to achieve this, the odorous substances have to "absorb" to the textiles. One difficulty in this regard is the fact that the "absorptive behavior" of many odorous substances differs from one another. Certain odorous substances have great difficulty clinging to specific fibers. Other odorous substances are so volatile that they soon re-evaporate from the fibers. Nevertheless, if the odorous substances are enclosed in microcapsules, the absorptive capacity is determined by the properties of the capsules, but not by the properties of the odorous substances.

For the perfuming of textiles and items of laundry with the aid of microcapsules in a washing process, it is in this case important that as high a proportion as possible of the capsules used clings to the textiles or the fibers thereof, i.e. absorbs to the woven fabrics. Specific surface properties of the capsules can promote this absorptive process.

In many cases, it is desirable if the microcapsules release the odorous substance or substances in a specific manner. When used in fabric softeners, as described hereinbefore, the capsules are to be substantially tight with respect to diffusion of the enclosed odorous substances in the fabric softener formulation—the aim is to prevent the odorous substances from diffusing out of the capsules when already in the fabric softener. In addition, the capsules have to have a certain mechanical hardness (or stability) to resist the mechanical loads during the washing and drying process (for example in a laundry dryer). The capsules should also endure drying-out per se without releasing the enclosed odorous substances. It should in turn be possible to open capsules absorbed to textiles by way of mechanical stressing: Under the mechanical movement when the laundry is being worn, individual capsules should where possible be opened and release perfume (odorous substances)—if appropriate a scent boost should even be discernible. For this purpose, it is advantageous if the walls display a certain brittleness, so that individual capsules can be opened by way of friction and pressure on the dry textiles.

In principle, different technologies are available for (micro)encapsulating odorous substances (enclosing in (micro) capsules). On the one hand, it is possible to produce, for example by spray-drying, matrix particles, i.e. particles in which tiny droplets of the odorous substances (odorous substance composition) are enclosed or dissolved in an amorphous matrix.

Higher charging with odorous substances can be obtained by core shell capsules. A core shell capsule has a defined shell (wall) surrounding an individual, defined compartment (the core) comprising ingredients. Typically, the core consists of a pure odorous substance composition, or the odorous substances are dissolved in a (usually nonpolar oil as the) solvent.

In core shell capsules, such as form the subject-matter of this invention, higher charging of the capsules with odorous substances (charge density) can be attained than in matrix particles.

A plurality of methods has been found to be suitable for the production of core shell microcapsules. In all conventional methods, a fine dispersion (conventionally an emulsion) of the perfume oil, which is optionally dissolved in a suitable solvent, is first produced in a (second) liquid phase. The drops of emulsion (or dispersed particles) form the core of the future capsule; their dimensions directly determine the size of the subsequent capsule cores.

In the majority of these methods, the components which form the future capsule wall emanate from the homogeneous phase surrounding the drops of emulsion (dispersed particles). These processes include coacervation, in particular complex coacervation and in-situ polymerization. The latter process is usually used for the production of aminoplast capsules (for example formaldehyde/urea capsules or melamine/formaldehyde capsules). Aminoplast capsules currently form the majority of industrial core shell products, for example for the encapsulation of odorous substances in fabric softener applications. The processes for the production thereof are known to a person skilled in the art. Nevertheless, both coacervation and in-situ polymerization have drawbacks in the production of capsules: Both methods are challenging to carry out, and they are in many cases insufficiently reproducible.

A technically simpler method for the production of core shell capsules is interfacial polymerization. In this case, at least two monomer or oligomer components react at phase interfaces. These are formed between a continuous phase and drops of emulsion distributed therein (or dispersed particles representing a second phase). At least one of the components is in this case contained in the continuous phase and at least one further of the components in the dispersed phase. As the components react with one another at the phase interface, the resultant polymer is already localized at the phase interface. A method of this type can therefore be carried out in a technically simple and reproducible manner. The capsules, such as form the subject-matter of the present invention, can be produced preferably by interfacial polymerization.

Suitable processes and materials for the production of microcapsules by interfacial reaction have long been known. Typical systems use the reaction between polyisocyanates and organic amines. Known from the 1970s are for example documents DE 2 251 381 A, DE 2 242 910 A and DE 2 120 921 A which disclose microcapsules used generally for the production of carbonless copy papers.

This technology has also been applied to the encapsulation of odorous substances.

The documents mentioned hereinafter disclose examples of the encapsulation of odorous substances by way of interfacial reaction between polyisocyanates and guanidine compounds. They illustrate prototypically the properties of microcapsules consisting of interfacial polymerizations. Advantages of the use of guanidine compounds include the odorlessness and non-toxicity of the guanidine compounds.

Microencapsulation by means of guanidine compounds and polyisocyanates was surely described for the first time in DE 195 01 479 A1. The properties of polyisocyanates were then specified in greater detail in documents DE 196 07 632 A1 (aliphatic, biuret group-containing polyisocyanates), DE 196 23 566 A1 (uretdione group-containing polyisocyanates) and DE 196 46 110 (oxadiazine isocyanates/iminooxadiazinedione). Specific applications of these microcapsules are described in DE 102 44 215 A1 (finishing of textile substrates with a microcapsule dispersion comprising a surfactant component; fragrance composition in capsules) and DE 101 17 671 A1 (leather containing fragrance-containing microcapsules). The actual use of microcapsules consisting of guanidine compounds and polyisocyanates for the perfuming of home or personal care applications is described in WO 2007/004166 A1.

A conventional process for the production of capsules (microcapsules) by means of interfacial reaction using isocyanates to produce the wall (the shell surrounding the core) will be described hereinafter. Conventionally, the substances to be encapsulated are (as required) in a first step dissolved in a hydrophobic, substantially inert oil and blended with (poly) isocyanates which are suitable for forming the wall.

In a second step, this (oil) phase is conventionally dispersed (preferably emulsified) in an aqueous phase. The droplets of oil of the resulting oil-in-water emulsion (or the particles of the dispersion) have in this case a size corresponding substantially to the size of the subsequent microcapsule. Conventionally, the aqueous phase of an emulsion contains protective colloids, for example polyvinyl alcohol, carboxymethylcellulose, emulsifiers and/or stabilizers, to prevent coalescing (mutual combining) of the oil phase.

In a third step, the oil-in-water emulsion is conventionally blended with a crosslinking agent for the isocyanates, which crosslinking agent becomes part of the aqueous phase. An interfacial reaction between the crosslinking agent and isocyanate leads to the formation of the capsule walls. In specific embodiments of the these steps, the crosslinking agent can also be present in the aqueous phase as early as in the second step. A fresh capsule dispersion is produced.

In a fourth step, the fresh capsule dispersion is conventionally subjected to a subsequent treatment: By controlling the temperature, residence time and if appropriate the use of further auxiliaries, the reaction is completed for hardening the capsule walls.

Nevertheless, as is apparent from the example of polyisocyanate/guanidine microcapsules, the prior-art capsules consisting of interfacial polymerizations of polyisocyanates with amines display the following drawbacks:

The scope of variation of the amine component used in the prior art is limited. In many cases, the properties of the capsules cannot be optimally adapted to the desired application.

The conventional diisocyanates and polyisocyanates containing more than two isocyanate groups are based on relatively long alkyl chains between the isocyanate functionalities. The polymer networks which can be obtained therefrom by crosslinking are therefore relatively coarse-meshed and have a high content of alkyl groups. This leads to the following properties which are not desirable for microencapsulation in this application:

Owing to the coarse mesh and the high alkyl group content of the polymer network, non-polar substances can diffuse effectively from the core of the capsules into the polymer network. The blocking effect for nonpolar substances therefore decreases. The shell swells up as a result of the immigration of the nonpolar substances, thus further reducing their blocking effect.

As a result of the coarse mesh, the elasticity (the elastomeric character) of the shell (wall) is relatively pronounced. In addition, immigrated nonpolar substances (in particular solvents) act like plasticizers: the elasticity and softness of the shell is further increased. This can adversely influence the absorptive capacity of the capsules.

The coarse mesh and also the elasticity or softness cause the shell to display only relatively low brittleness. Under mechanical loading, the shell tends more to be elastically deformed than to break up in a brittle manner. This can adversely influence the desired release behavior under mechanical stressing.

Particularly nonpolar and/or aromatic substances (for example solvents) can soften the polymer network and thus the capsule shell, after diffusing-in as a result of swelling and as a result of loosening of the polymer network, to the extent that the shell dissolves even without or under only slight mechanical loading. Some nonpolar phases (oil phase) cannot be encapsulated at all, as the capsule wall softens or dissolves in the non-polar phase.

In the prior art, specific diamines or polyamines have already been proposed as alternatives to guanidine. These are generally compounds such as diethylenetriamine, polyethyleneimine or polyether diamines (such as for example the Jeffamines from Huntsman). However, these amines have for their part a certain alkyl group content in the carrier skeleton. Therefore, they reinforce the above-described coarse mesh and the lipophilia of the polymer network. The described undesirable effects can therefore be further intensified.

From an economic perspective, it is desirable to use as small amounts as possible of the amine component (crosslinking agent for the isocyanate component). In principle, it is even possible to construct polymer networks exclusively based on the reaction of polyisocyanates (including diisocyanates) with water: Certain contents of the isocyanate component react in this case with water under decarboxylation to form amines which react with the remaining isocyanates, with the formation of urea functionalities, to form polymer networks. However, in independent tests, it was not possible to obtain capsules having the desired properties merely from the reaction of polyisocyanates with the water of the homogeneous phase.

Alternatively, polyols of low molecular weight (for example diols) can be added to the water phase, leading, on reaction with an isocyanate function, to the formation of urethanes. However, capsules of this type conventionally have lower diffusion density than the capsules for the production of which guanidine was used as the crosslinking agent.

Nevertheless, from an economic perspective, a use of high contents of the amine component, such as for example just below the stoichiometric amounts in stoichiometric amounts or even thereabove (in each case based on the contents of isocyanate groups), is disadvantageous.

The primary object of the present invention was to specify an alternative to the above-described capsules of the prior art. Preferably, the capsules to be specified should have (at in each case the same wall thickness) higher stability and/or hardness with respect to shear and compressive forces than the capsules of the prior art, in particular on use of substoichiometric amounts of amine component in relation to the isocyanate component. Also advantageous are capsules which are damaged as little as possible as a result of drying-up, in particular in the case of capsules formed using substoichiometric amounts of amine component in relation to the isocyanate component. Also advantageous are components for polymeric materials allowing a broad scope of variation with regard to the construction of the capsule shell, thus allowing the capsule shell to be adapted as effectively as possible to the desired application. It is a particular object of the present invention to specify capsules which can be produced while reacting a polyisocyanate with an amine component, wherein the properties of the resulting polymeric materials can be set in a further and/or different range to that in the case of the amine components previously used for this purpose. This amine component should be preferably water-soluble and in particular accessible as oligomers or prepolymers in a procedurally simple manner, so that its properties, such as for example water-solubility or reactivity with respect to isocyanates, can be set in broad ranges.

Surprisingly, it has been found that the primary and further objects are achieved by a capsule, comprising or consisting of a core and a shell surrounding the core, wherein the shell comprises a polymeric material or consists thereof, which polymeric material can be produced by reacting a component (A) with a component (B), wherein component (A) consists of polysiloxanes bearing one or more amino groups and component (B) consists of one or more polyisocyanates.

Particularly outstanding results, even compared to the prior art, are achieved by the capsules according to the invention, in particular the capsules designated hereinafter as being (particularly) preferred, in the following areas:

- there are attained, in particular as a result of a use of a corresponding component (A), polymer networks having advantageous properties with regard to a low content of alkyl groups and/or their close mesh (or regions linked with close mesh in their skeletal structures);
- low lipophilia of the shell;
- good blocking effect of the shell, in particular with respect to nonpolar substances;
- good absorptive capacity of the capsule, in particular to conventional textile fabrics;
- good elasticity and/or softness of the shell or the possibility of exactly setting the elasticity and/or the softness;
- high dimensional and/or weight stability of the capsule during storage, in particular high stability with respect to shear and compressive forces;
- high brittleness;
- the possibility of encapsulating markedly nonpolar and/or aromatic substances, such as for example solvents, in particular without the shell softening or dissolving in these substances;
- the possibility of using a stoichiometrically low content of an amine component based on an isocyanate component, in particular without losing the advantageous properties of the capsules;
- complete encapsulating of ingredients, so that substantially no unencapsulated ingredients remain;
- odorlessness and/or biocompatibility (in particular non-toxicity) of an amine component to be used or the resulting capsule.

Preferably, the polymeric material of the shell of a capsule according to the invention is produced by reacting component (A) with component (B) as defined above. Capsules having preferred properties are in particular obtained if amino group-bearing polysiloxanes are used as crosslinking agents for polyisocyanates.

It is preferred for the at least one of or all of the amino group-bearing polysiloxanes of component (A) to bear two or more amino groups. This allows crosslinking of the polymeric material. Crosslinking is however also possible using polysiloxanes comprising silicon atoms which are bound to more than two (i.e. to three or four) O atoms which are in turn bound to further Si atoms (i.e. are T and Q modules).

The properties of the capsule according to the invention in relation to the release of the core constituents and also the capacity thereof for absorption to specific substrates can be specifically set within broad limits, in particular owing to a use of amino group-bearing polysiloxanes (as the crosslinking agent of a polyisocyanate component). A use of this type also allows the use of different amino group-bearing monomers for the production of the amine component and thus very high variability.

A capsule according to the invention (in particular as described hereinbefore) may be described using structural features as follows:
capsule, comprising or consisting of a core and a shell surrounding the core, wherein the shell comprises a polymeric material or consists thereof, which polymeric material comprises groups of structure G1:

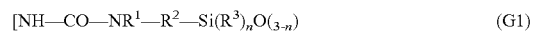

$$[NH-CO-NR^1-R^2-Si(R^3)_nO_{(3-n)}] \quad (G1)$$

and also optionally of structure G2

$$[NH-CO-NH] \quad (G2)$$

wherein the following applies:
$R^1$ is selected from the group consisting of H, if appropriate $NH_2$-substituted unbranched alkyl, if appropriate $NH_2$-substituted branched alkyl and if appropriate $NH_2$-substituted cycloalkyl;
$R^2$ is an organic linker, preferably an unsaturated or saturated hydrocarbon and preferably an unbranched or branched alkylene;
$R^3$ is selected from the group consisting of unbranched or branched alkyl and cycloalkyl;
n=0 or 1 and
each O atom bound directly to the Si atom of G1 is bound directly to a further Si atom.

Preferably, the polymeric material can be produced by reacting a component (A) with a component (B), wherein component (A) consists of one or more corresponding amino group-bearing polysiloxanes and component (B) consists of one or more corresponding polyisocyanates. With regard to preferred production processes according to the invention, see below.

Preferably, the group of structure G1 is a group of structure G1'

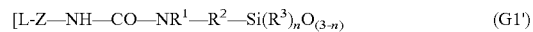

$$[L-Z-NH-CO-NR^1-R^2-Si(R^3)_nO_{(3-n)}] \quad (G1')$$

and/or the group of structure G2 is a group of structure G2'

$$[L-Z-NH-CO-NH-Z-L] \quad (G2'),$$

wherein the following applies:
L is selected from the group consisting of

CO—NH—,

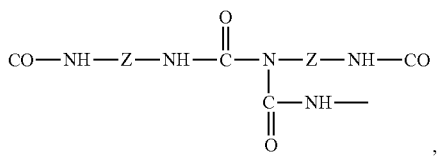

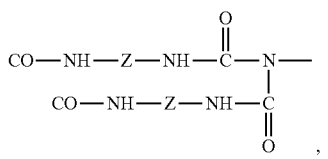

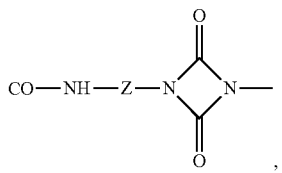

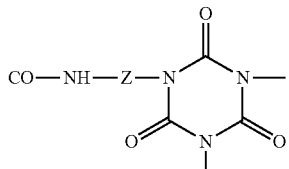

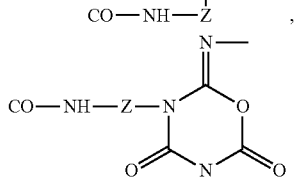

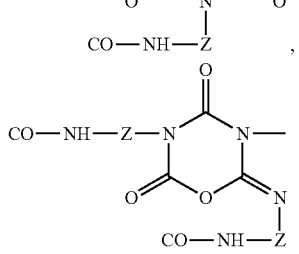

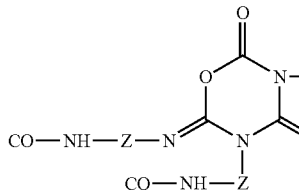

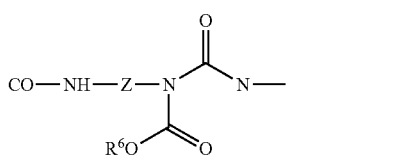 und $$\text{CO—NH—Z—N}\underset{R^6O}{\overset{O}{\bigg\langle}}\overset{O}{\underset{O}{\bigg\rangle}}\text{N—}$$

[und = and]

$R^9$ is a hydrocarbon group containing 1 to 10 carbon atoms, preferably n-butyl or a different alkyl;

Z is a hydrocarbon group which is optionally singly or multiply substituted by —NH—CO-groups bound via the N atom, wherein the groups are each connected to an —NR$^1$—R$^2$—Si atom group or an —NH—Z atom group via their C atom.

The groups of structure G1 and G2 are urea derivative structures and are not repeating units, but structurally characteristic units which are contained in a corresponding polymeric material and can serve to describe the material more precisely. G1 and G2 each describe a structure which emanates from the reaction of a polyisocyanate with a reactant which is, in the case of G1, an amino group-bearing polysiloxane and, in the case of G2, a decarboxylation product of a corresponding polyisocyanate. The simplest polyisocyanate to be used is a diisocyanate of formula OCN—Z—NCO.

Groups of structures G1 and G2 occur inside the polymeric material. In particular at the points at which the groups G1 and G2 are delimited in the foregoing formula notation by a square bracket, further covalent bonds are therefore connected. Therefore, the terminal carbonyl groups in the foregoing list of individual groups L are therefore also to be understood to mean that a further covalent bond is connected to their respective carbon atom. The point at which the nitrogen atom of a specific group L is linked to Z is marked in each case by a terminal horizontal dash.

Preferred is a capsule according to the invention as defined hereinbefore (according to the definition without structural features or according to the definition with structural features), wherein the reaction is an interfacial reaction in which a first phase comprising component (A) and a second phase comprising component (B) are contacted.

The above-mentioned prior-art documents do not disclose any polysiloxane.

The reaction between amino group-bearing polysiloxanes and isocyanates is in principle known. Thus, block copolymerization between amino group-bearing polysiloxanes (aminopolysiloxanes) and isocyanates has been described repeatedly, albeit in batch processes, for example in EP 0 250 248 A2. This document does not disclose any interfacial polymerization (interfacial reaction) or any capsule. In particular, there is disclosed no encapsulation based on interfacial polymerization between isocyanates and aminopolysiloxanes.

The regions of the polymeric material originating from the aminopolysiloxane often tend to be hard, while the regions originating from the polyisocyanate often tend to be soft and resilient. The desired properties of the shell may thus be set as desired depending on the area of application.

Preferred is a capsule as defined hereinbefore (according to the definition without structural features or the definition with structural features), wherein the reaction is an interfacial reaction in which a first phase comprising component (A) and a second phase comprising component (B) are contacted, wherein during the interfacial reaction the second phase is dispersed, preferably emulsified, in the first phase and comprises, in addition to component (B), also one or more further ingredients of the core.

Preferably, the further ingredient or ingredients are in this case chemically inert with respect to component (B).

Preferred is a capsule according to the invention as defined hereinbefore (in particular according to one of the preferred embodiments), wherein (i) the amino group-bearing polysiloxanes of component (A) are water-soluble and/or (ii) the polyisocyanates of component (B) are water-insoluble.

A capsule according to the invention is preferred (in particular according to a preferred embodiment), wherein during the reaction (i) the amino group-bearing polysiloxanes of component (A) are present in the form of an aqueous solution or an aqueous colloid and/or (preferably and) (ii) the polyisocyanates of component (B) are present in the form of a dispersion in water.

The aminopolysiloxanes are generally accessible by hydrolysis and condensation of aminoalkylsilanes (in particular aminoalkylalkoxysilanes) containing hydrolyzable groups. If appropriate, condensation can be carried out using further silanes containing hydrolyzable groups (for example alkoxy groups) and optionally additionally non-hydrolyzable groups (for example alkyl groups), i.e. in particular using alkoxysilanes and/or alkylalkoxysilanes. Conventionally, a stoichiometrically required amount of water is in this case added for the purposes of hydrolysis and by-products (for example alcohol) produced during the condensation reaction are removed by distillation.

By appropriately selecting the aforementioned silane components, which can be present for example as monomers and/or oligomers, a person skilled in the art can purposefully set the properties of the condensation products. The more silanes comprising four hydrolyzable groups (for example tetraalkoxysilanes) are used as condensation partners for the amino group-containing siloxanes, the more water-soluble the condensation products are. The additional incorporation of silanes containing, in addition to hydrolyzable groups, also non-hydrolyzable, more hydrophobic groups (for example alkyl groups) leads to increasingly hydrophobic condensation products.

Preferred is a capsule according to the invention as defined hereinbefore (in particular according to a preferred embodiment), wherein the amino group-bearing polysiloxanes of component (A) can be produced, preferably are produced by a process including the following steps:
providing or producing the following compounds:
(a) one or more aminoalkylalkoxysilanes of formula (I)

$$R^1\text{—NH—}R^2\text{—Si}(R^4)_x(X^1)_{3-x} \qquad (I),$$

(b) if appropriate one or more further silanes of formula (II)

$$\text{Si}(R^5)_y(X^2)_{4-y} \qquad (II),$$

wherein the following applies:
$R^1$ is selected from the group consisting of H, if appropriate $NH_2$-substituted unbranched alkyl, if appropriate $NH_2$-substituted branched alkyl and if appropriate $NH_2$-substituted cycloalkyl,
$R^2$ is an unbranched or branched alkylene,
$R^4$ is selected from the group consisting of unbranched or branched alkyl and cycloalkyl,
each $X^1$ is, independently of each further $X^1$, a hydrolyzable group,
each $R^5$ is, independently of each further $R^5$ which may be present, selected from the group consisting of unbranched or branched alkyl and cycloalkyl,
each $X^2$ is, independently of each further $X^2$, a hydrolyzable group,
x=0 or 1,
y=0, 1 or 2,
producing an aqueous solution of the aforementioned compounds (according to (a) and if appropriate (b)),
setting or ensuring conditions under which the hydrolyzable groups are hydrolyzed, preferably by setting a pH in the range between 3 and 11,
removing compounds $HX^1$ and $HX^2$ from the mixture.
It is particularly preferred if, for the compounds of formulae (I) and (II), the following applies:
$R^1$ is selected from the group consisting of H; if appropriate $NH_2$-substituted unbranched alkyl; if appropriate $NH_2$-substituted branched alkyl containing 1 to 8, preferably 1 to 3 C atoms and cycloalkyl containing 3 to 6, preferably 6 C atoms,
$R^2$ is an unbranched or branched alkylene containing 1 to 8 C atoms, preferably 1 to 3 C atoms,
$R^4$ is selected from the group consisting of unbranched or branched alkyl containing 1 to 8, preferably 1 to 3 C atoms and cycloalkyl containing 3 to 6, preferably 6 C atoms,
each $X^1$ is, independently of each further $X^1$, an alkyloxy containing 1 to 4 C atoms,
each $R^5$ is, independently of each further $R^5$ which may be present, selected from the group consisting of unbranched or branched alkyl containing 1 to 8, preferably 1 to 3 C atoms and cycloalkyl containing 3 to 6, preferably 6 C atoms,
and/or
each $X^2$ is, independently of each further $X^2$, an alkyloxy containing 1 to 4 C atoms.

The above-cited groups of structure G1 bear radicals $R^3$. These correspond to the groups $R^4$ of the aforementioned aminoalkylalkoxysilanes and if appropriate the groups $R^5$ of the aforementioned further silanes. The radicals $R^1$ and $R^2$ of the groups of structure G1 correspond to the radicals $R^1$ and $R^2$ of the aforementioned aminoalkylalkoxysilanes.

The setting of parameters in the particularly preferred ranges specified for the compounds of formulae (I) and (II) makes it particularly easily possible to obtain capsules according to the invention having the above-specified advantageous properties.

Particularly suitable in the sense of the invention are aminopolysiloxanes which are dissolved in water and are not present as gel.

Aminofunctional organosiloxanes are known from EP 0 675 128 A1 (Hüls 1994) and EP 0 716 128 A1 (Hüls 1995). These organosilane systems are almost completely hydrolyzed and the products of the hydrolysis are miscible with water. DE 198 49 308 A1 (Hüls 1998) describes the synthesis of aminopropyl-functional siloxane oligomers by partial hydrolysis of aminosiloxanes, alkyltrialkoxysilanes and tetraalkoxysilanes in aqueous/alcoholic solution, wherein chain and annular oligomers are obtained.

These documents do not disclose a capsule or interfacial polymerization.

The amino group-bearing polysiloxanes of component (A) can be produced and preferably are produced by a process including the above-mentioned steps. When producing the aforementioned solution, the compound(s) and if appropriate the mixing ratio are preferably selected in such a way that the process allows the production of water-soluble aminopolysiloxanes.

The compounds $HX^1$ and $HX^2$ are preferably removed from the mixture by distillation and are, according to a preferred embodiment, alcohols.

A preferred amino group-bearing polysiloxane (aminopolysiloxane, crosslinking agent) can be obtained for example by acid hydrolysis of (3-aminopropyl)triethoxysilane and subsequent condensation, in that ethanol is removed from the reaction by distillation. The obtained aqueous solution of the aminopolysiloxane can be used directly for crosslinking.

Preparations of suitable aminopolysiloxanes are also commercially available. Within the scope of the present invention, aminopolysiloxanes dissolved in water from Evonik having the names Dynasylan Hydrosil 1151, Dynasylan Hydrosil 2627, Dynasylan Hydrosil 2776 are preferred.

The equivalent weight of a polymer is the mass of polymer that 1 mol of reactive functional groups has bound to the polymer backbone. The manner in which the equivalent weight is to be calculated is known to a person skilled in the art. In order to calculate the amounts to be used of compounds of components (A) and (B) which he uses to produce the polymeric material of the shell of a capsule according to the invention, a person skilled in the art will take into account in the conventional manner the equivalent weight of the aminopolysiloxane or aminopolysiloxanes used and of the polyisocyanate or polyisocyanates used.

In order to react all isocyanate groups located in the oil phase (second phase), in theory the same number of amino groups is required. Therefore, it is sometimes advantageous to use the isocyanate and the amine component (in the form of aminopolysiloxanes) in the ratio of their equivalent weights. It is however also possible, and within the scope of this invention often preferred, to use non-equivalent amounts. The amount of crosslinking agent can be either greater than or less than the stoichiometrically calculated (functionally equivalent) amount. Particularly preferably, the amino component is used substoichiometrically, as a result of which excess isocyanate reacts in a secondary reaction with the water of the homogeneous phase (first phase) by decarboxylation to form amino groups. These lead with isocyanates to further crosslinking of the capsule wall.

Preferred is a capsule according to the invention as defined hereinbefore (in particular in a preferred embodiment), wherein in component (A) use is made of 0.2 to 4 mol, preferably 0.2 to 1.8 mol, particularly preferably 0.2 to 1 mol and most particularly preferably 0.2 to 0.9 mol of amino groups per 1 mol of isocyanate groups present in component (B). A capsule according to the invention having advantageous properties can be obtained in particular if, based on the number of isocyanate groups, a lower number of amino groups is used.

The properties of the capsules according to the invention can be influenced not only by the selection of the aminopolysiloxanes of component (A), but also by the selection of the isocyanate component (polyisocyanates of component (B)). In particular, this is possible by way of the number of reactive groups (of isocyanate groups) per polyisocyanate.

Preferred is a capsule according to the invention as defined hereinbefore (preferably in one of the embodiments characterized as being preferred), wherein the polyisocyanate or polyisocyanates of component (B) comprise two or more isocyanate groups per molecule and are preferably selected from the group consisting of hexamethylene diisocyanate, isophorone diisocyanate and/or derivatives thereof, wherein each of these derivatives comprises two or more isocyanate groups and contains one or more groups selected from the group consisting of biuret, isocyanurate, uretdione and iminooxadiazinedione.

Preferably, the polyisocyanates of component (B) comprise for each molecule 2, 3, 4, 5 or 6 isocyanate groups, preferably 2, 3 or 4 and particularly preferably 2 or 3 isocyanate groups.

Preferred polyisocyanates of component (B) are the industrially available polyisocyanates hexamethylene diisocyanate (HDI), isophorone diisocyanate (IPDI), toluene diisocyanate (TDI) and diphenylmethane diisocyanate (MDI) and derivatives thereof, wherein that which was stated hereinbefore applies to the derivatives. For producing the capsules according to the invention, aliphatic polyisocyanates, in particular HDI and IPDI and derivatives thereof, are preferred, as the aliphatic polyisocyanates display less activity than the aromatic polyisocyanates, over a longer processing time, and higher light-fastness.

Even the monomeric diisocyanates (for example diisocyanates of formula OCN—Z—NCO, in particular the aliphatic diisocyanates such as for example HDI and IPDI) can be used for encapsulations with aminopolysiloxanes in the sense of this invention. Nevertheless, owing to their lower toxicity and their lower steam pressure, condensates (oligomers) of these diisocyanates are frequently preferred. These are in particular the trimers (for example of HDI), such as the biurets (for example the commercial products Desmodur N100 and Desmodur N3200; manufacturer of the Desmodur products: Bayer MaterialScience), the isocyanurates (for example of HDI such as Desmodur N3300 and Desmodur N3600 having a lower oligomer content) and the iminooxadiazinediones (for example of HDI such as Desmodur XP 2410) and the dimers (for example of HDI), such as the uretdiones (for example Desmodur 3400) and the corresponding allophanates.

Examples of corresponding compounds of IPDI include the trimer of IPDI (for example Desmodur Z4470BA).

The use of polyisocyanates comprising more than two isocyanate groups increases the degree of crosslinking and thus in many cases the close mesh of the polymeric material.

The content of polyisocyanates, also referred to as the wall content (shell content), in the second phase (conventionally the oil phase) is within the range which is conventional for interfacial polyadditions, for example between 2 and 20% by weight, based on the mass of the entire second phase. A wall content in the range of between 4 and 15% by weight is preferred.

Preferably, a capsule according to the invention has, as defined hereinbefore (preferably in a preferred embodiment), a diameter of from 1 to 500 µm, preferably 2 to 50 µm.

As stated above, the shell of a capsule according to the invention is produced preferably while reacting a component (A) with a component (B), wherein the second phase comprises, in addition to component (B), also one or more further ingredients of the core. These further ingredients form the crucial content of the future capsule cores. The further ingredients comprise preferably one or more active substances and if appropriate one or more solvents. Preferably, the further ingredients are, as stated, chemically inert with respect to the isocyanates; that is to say, they do not react with them. Preferably, the further ingredients are not alcohols (or at least not primary alcohols) and/or not amines. It is preferable to select hydrophobic active substances and/or solvents which are not miscible with water.

Preferred is a capsule according to the invention as defined hereinbefore (preferably in a preferred embodiment), wherein the core contains one or more further ingredients selected from the group consisting of an odorous substance, dye, dye precursor, catalyst for chemical reactions, adhesive, reactive substance for adhesive applications, pharmaceutical active substance, cosmetic active substance, plant protection active substance (for example insecticide, fungicide, herbicide), water repellent, flame retardant and solvent.

Conceivable active substances generally include all compounds for which there exist applications from the field of microencapsulation. Examples include, for instance, color definers for the production of carbonless copy papers, and medicines for pharmaceutical applications. Active substances for cosmetic applications are preferred.

Also preferred are active substances which are odorous substances or odorous substance compositions, in particular for application in and/or perfuming of consumer goods. Either an individual odorous substance or a mixture of odorous substances (perfume composition, odorous substance composition) can be selected. The odorous substances can be compounds both of synthetic and of natural origin.

Detailed examples of perfume constituents of this type are known from the literature, for example from the book "Perfume and Flavor Chemicals", edited by S. Arctander, 1969, Montclair N.J. (USA).

When setting the odorous substance composition for the encapsulation application, it should be borne in mind that individual odorous substances can react, in particular with the isocyanates. This is the case in particular in the substance group of the alcohols. Preferably, the use of alcohols will therefore be (wholly or at least substantially) dispensed with when setting the odorous substance composition; the odorous substance composition is preferably free from alcohol.

Preferred is a capsule according to the invention as defined hereinbefore (preferably in a preferred embodiment), wherein the core contains one or more odorous substances selected from the group consisting of extracts of natural raw materials such as essential oils, concretes, absolutes, resins, resinoids, balsams, tinctures such as for example ambergris tincture; amyris oil; angelica seed oil; angelica root oil; aniseed oil; valerian oil; basil oil; tree moss absolute; bay oil; armoise oil; benzoin resin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; fir needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue chamomile oil; Roman chamomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi bark oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Pew balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil: spike-lavender oil; star anise oil; styrax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniper berry oil; wine lees oil; wormwood oil; wintergreen oil; ylang-ylang oil; hyssop oil; civet absolute; cinnamon leaf oil; cinnamon bark oil, and also fractions thereof, or ingredients isolated therefrom;

individual odorous substances from the group of the hydrocarbons, such as for example 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

aliphatic aldehydes and acetals thereof such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethyl acetal; 1,1-dimethoxy-2,2,5-trimethyl-4-hexene; citronellyloxyacetaldehyde; 1-(1-methoxypropoxy)-(E/Z)-3-hexene;

aliphatic ketones and oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate, in particular ethyl-2-trans-4-cis-decadienoate; methyl-2-octinate; methyl-2-noninate; allyl-2-isoamyloxyacetate; methyl-3,7-dimethyl-2,6-octadienoate; 4-methyl-2-pentyl crotonate;

formates, acetates, propionates, isobutyrates, butyrates, isovalerates, pentanoates, hexanoates, crotonates, tiglinates or 3-methyl-2-butenoates of acyclic terpene alcohols such as for example citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol;

acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranyl acetone and also dimethyl and diethyl acetals thereof; in particular the dimethyl and diethyl acetals of geranial, neral, 7-hydroxy-3,7-dimethyloctanal;

formates, acetates, propionates, isobutyrates, butyrates, isovalerates, pentanoates, hexanoates, crotonates, tiglinates and 3-methyl-2-butenoates of cyclic terpene alcohols such as for example menthol; isopulegol; alpha-terpineol; terpinenol-4; menthan-8-01; menthan-1-ol; menthan-7-ol; borneol; isoborneol; linalool oxide; nopol; cedrol; ambrinol; vetiverol; guaiol;

cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one, alpha-sinensal; beta-sinensal; acetylated cedar wood oil (methylcedryl ketone);

cyclic and cycloaliphatic ethers such as for example cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

cycloaliphatic aldehydes such as for example 2,4-dimethyl-3-cyclohexene carbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl) ketone;

esters of cyclic alcohols such as for example 2-tert.-butylcyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols such as for example 1-cyclohexylethyl crotonate;

esters of cycloaliphatic carboxylic acids such as for example allyl-3-cyclohexyl propionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane-2-acetate;

esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers such as for example 2-phenyl ethyl methyl ether; 2-phenyl ethyl isoamyl ether: 2-phenyl ethyl-1-ethoxyethyl ether; phenyl acetaldehyde dimethyl acetal; phenyl acetaldehyde diethyl acetal; hydratropaldehyde dimethyl acetal; phenyl acetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as for example benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butyl phenyl)propanal; 2-methyl-3-(4-isobutlyphenyl)propanal; 3-(4-tert.-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as for example acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3,5,5,6,8,8-hexamethyl-2-acetonaphthone;

aromatic and araliphatic carboxylic acids and esters thereof such as for example benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogen-containing aromatic compounds such as for example 2,4,6-trinitro-1,3-dimethyl-5-tert.-butylbenzene; 3,5-dinitro-2,6-dimethyl-4-tert.-butyl acetophenone; cinnamonitrile; 3-methyl-5-phenyl-2-pentenoic acid nitrile; 3-methyl-5-phenylpentanoic acid nitrile; methyl anthranilate; methyl-N-methyl anthranilate;

Schiff bases of methyl anthranilate with 7-hydroxy-3,7-dimethyloctanal, 2-methyl-3-(4-tert.-line; 6-isobutyl quinoline; 6-sec.-butyl quinoline; 2-(3-phenylpropyl) pyridine; indole; skatole; 2-methoxy-3-isopropylpyrazine; 2-isobutyl-3-methoxypyrazine;

phenyl ethers and phenyl esters such as for example estragole; anethole; eugenyl methyl ether; isoeugenyl methyl ether; diphenyl ether; beta-naphthyl methyl ether; beta-naphthyl ethyl ether; beta-naphthyl isobutyl ether; 1,4-dimethoxybenzene; eugenyl acetate; p-cresyl phenyl acetate;

heterocyclic compounds such as for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one; and lactones such as for example 1,4-octanolide; 3-methyl-1,4-octanolide; 1,4-nonanolide; 1,4-decanolide; 8-decen-1,4-olide; 1,4-undecanolide; 1,4-dodecanolide; 1,8-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; coumarin; 2,3-dihydrocoumarin; octahydrocoumarin;

wherein the shell is completely or substantially impervious to the odorous substance or substances and wherein preferably the odorous substance or substances are chemically inert with respect to component (B).

Preferred solvents are in particular organic compounds which are not miscible with water and do not react with the isocyanate components, for example alkyl aromatic hydrocarbons such as diisopropylnaphthalene or substituted biphenyls, paraffins, natural oils (for example sunflower oil) and low-melting fats (such as coconut oil).

For cosmetic applications or the encapsulation of odorous substances, preference is given in particular to those solvents which are used broadly in the perfume industry (except for alcohols which react with the isocyanates). Examples of solvents preferred for this purpose include phthalates (such as diethyl phthalate), isopropyl myristate, benzyl benzoate, ethyl citrate, limonene or other terpenes and isoparaffins.

The concentration of the active substances in the second phase as defined above (conventionally the oil phase) can be varied within broad ranges depending on the active substance and application. For example, in cosmetic applications, contents of from 0.1 to 10% by weight of the active substance based on the total amount of the oil phase may be preferred, whereas hydrophobic, liquid active substances (for example for industrial applications) can be used directly without the addition of inert solvents.

A broad concentration range is possible also for the preferred application in perfume oils (perfume compositions). Thus, for specific applications, it may be beneficial to use the perfume oil only in amounts of from 10 to 20% by weight as a solution in a nonpolar, inert solvent. This reduces the release of the odorous substance components by way of diffusion through the capsule walls.

In other applications, it may (inter alia for economic reasons) be desirable to charge the capsules with as many odorous substances as possible. In these cases, the content of solvent in the oil phase should be less than 30% by weight. Preferred in these cases is a content of less than 20% by weight of the hydrophobic solvents at the oil phase, particularly preferred of less than 10% by weight. It is in these cases especially preferred if the (hydrophobic) second phase consists only of perfume constituents, i.e. is free from solvents.

A further aspect of the present inventions relates to a product, in particular a consumer goods product, comprising a capsule as claimed in any one of the preceding claims.

Preferred is a consumer goods product according to the invention that is selected from the group consisting of personal care product, home care product and laundry care product, is preferably selected from the group consisting of body care product, hair care product and laundry care product and is particularly preferably selected from the group consisting of shampoo, liquid washing agent and fabric softener.

Preferably, the consumer goods product is a detergent-containing preparation.

The introduction described a process which is conventional in the prior art for the production of capsules by means of interfacial reaction using isocyanates for producing the wall. A process of this type can also be used accordingly for the production of the capsules according to the invention.

According to a further aspect, the present invention relates to a process for the production of a capsule according to the invention as defined hereinbefore (preferably in a preferred configuration), including the following steps:

providing one or more substances to be encapsulated, one or more polyisocyanates and optionally a solvent, preferably an oil, wherein the aforementioned substances are adapted to one another in such a way that it is possible to produce therefrom a solution which is not soluble in water, providing or producing polysiloxanes bearing one or more amino groups, producing a solution (1) comprising the substance or substances to be encapsulated, the polyisocyanate or polyisocyanates and if appropriate the solvent, producing a dispersion of solution (1) in an aqueous solution or an aqueous colloid of the polysiloxane or polysiloxanes, allowing the reaction to proceed between the polyisocyanate or polyisocyanates and the polysiloxane or polysiloxanes, optionally subsequently maintaining the temperature in a range of from 40 to 80° C. for 0.5 to 5 hours.

When preparing solution (1), use is preferably made of an amount of polyisocyanates such as emerges from the foregoing discussion concerning the wall content. If solution (1) contains ingredients (for example active substances) which are capable of reacting with the isocyanate, the procedure should be continued immediately with the following step (producing a dispersion of solution (1)), so that kinetically interfacial polymerization (interfacial reaction) is preferable over the reaction of the active substances with the isocyanate. The dispersion of solution (1) is preferably an emulsion.

The emulsifying process can take place using high-power dispersing apparatuses by means of the rotor/stator principle; however, specific static mixers can also be used in the flow process.

For the subsequent size distribution of the capsule dispersion, it is important to set the size distribution of the emulsion (dispersion) accordingly. This variable can be measured using conventional light-scattering methods.

It is also important to protect the present emulsion (or generally dispersion) from coalescence. For this purpose, an emulsion is protected by the addition of emulsifiers; protective colloids are used in a dispersion. Examples of suitable protective colloids are polyvinyl alcohol(s), cellulose derivatives such as hydroxyethylcellulose or carboxymethylcellulose, polyethylene oxides and copolymers, for example of acrylamide and acrylic acid. The emulsifiers used may be anionic surfactants such as sodium dodecyl sulfate or nonionic surfactants such as polyethylene/polypropylene block copolymers. Optionally, further stabilizers are also used.

Optionally, it is first possible to produce an emulsion (or dispersion) of solution (1) in water or an aqueous solution which does not yet contain any polysiloxanes. The polysiloxanes are in this case added subsequently, preferably in the form of an aqueous solution.

The polyisocyanate-containing solution (1) is the above-mentioned second phase which is dispersed, preferably emulsified, in the aqueous solution or the aqueous colloid of the aminopolysiloxane or aminopolysiloxanes (of the first phase). This initiates an interfacial reaction (interfacial polymerization) between the polyisocyanates and the aminopolysiloxanes; the incipient crosslinking, forming polyureas, leads to the formation of an initially still thin wall around the drops of emulsion or dispersed particles.

In order to attain a high rate of reaction between the aminopolysiloxanes added and the polyisocyanates, the polysiloxanes should be present in the first phase already during or immediately after production of the emulsion (or dispersion) of solution (1). Otherwise, the isocyanate groups would react with the water, with decarboxylation; as stated above, this does not lead to the formation of stable capsule walls.

Preferred amounts of the aminopolysiloxane used emerge from the foregoing discussion concerning the molar ratio of the amino groups of component (A) to the isocyanate groups of component (B).

Stoichiometric use yields stable (dimensionally stable) capsule walls which also withstand particularly effectively mechanical loading caused by shear or compressive forces, even after drying-up.

The aminopolysiloxane contains, in addition to aminoalkyl groups, if appropriate further alkyl groups. The dimensional stability and brittleness of the capsule wall increases, the lower the content of these further alkyl groups is.

Independent tests have revealed that the aminoalkylsilanes can be used substoichiometrically (compared to the amount used of isocyanate groups). It is thus possible, for example, to carry out stable encapsulation with 0.2 equivalent weights of aminosiloxane. In this case, it is advantageous, for constructing a stable wall (shell), to carry out the optional process step mentioned last above (maintaining the temperature in the range of from 40 to 80° C. for 0.5 to 5 hours), particularly preferably at a relatively high temperature, for example in the range of from 60-80° C. and/or for a relatively long time, for example 2 to 5 hours. This may be due to the fact that the wall which is produced first, consisting of an organic/inorganic polyurea/composite compound, prevents the further admission of aminopolysiloxanes. However, moisture can still seep through the wall, so that the decarboxylation of the isocyanate groups to form amino groups continues. In addition to the primary wall, further wall constituents are formed. As a result of the secondary reaction of the newly formed amino groups with the isocyanates and the resulting further crosslinking of the wall, the wall is reinforced further.

As stated hereinbefore, in independent tests, it was not possible to produce stable capsules using just 0.2 equivalents of guanidine (compare in this regard Example 12).

Maintaining the temperature in the range of from 40 to 80° C. for 0.5 to 5 hours intensifies and/or completes the hardening of the shell. In this step, auxiliaries are optionally also used.

In the case of the stoichiometric use of aminopolysiloxanes, this optional process step may be dispensed with, or it is sufficient to carry it out for a shorter time and/or at lower temperatures. Stable capsules can be obtained, for example, during stirring for one hour at room temperature (for example with Dynasylan Hydrosil 2627 or with Dynasylan Hydrosil 2776). Alternatively, 0.5 hour at 50° C. may be sufficient.

Generally, in independent tests, mechanically stabler capsule walls were obtained when using aminopolysiloxanes to produce the capsules according to the invention than when using other amine components, for example guanidine (cf. Example 4).

A further aspect of the present invention relates to the use of a capsule according to the invention as defined hereinbefore (preferably in one of the configurations designated hereinbefore as being preferred) for perfuming a product. Preferred products result from that which was stated above with regard to the products according to the invention.

Further aspects of the present invention are apparent from the examples, the figures and the claims.

DESCRIPTION OF THE FIGURES

FIG. 1: polyisocyanate: Desmodur N3300, crosslinking agent: Hydrosil 1151, solvent: isopropyl myristate; capsules according to the invention; magnification lens: 100×

FIG. 2: polyisocyanate: Desmodur N3300, crosslinking agent: guanidine carbonate, solvent: isopropyl myristate; capsules not according to the invention; magnification lens: 100×

FIG. 3: polyisocyanate: Desmodur XP2410, crosslinking agent: Hydrosil 1151, solvent: benzyl benzoate; capsules according to the invention; magnification lens: 100×

FIG. 4: polyisocyanate: Desmodur XP2410, crosslinking agent: guanidine carbonate, solvent: benzyl benzoate; capsules not according to the invention; magnification lens: 100×

FIG. 5: polyisocyanate: Desmodur N3300, crosslinking agent: Hydrosil 1151, solvent: benzyl benzoate; capsules according to the invention; magnification lens: 10×

FIG. 6: polyisocyanate: Desmodur N3300, crosslinking agent: guanidine carbonate, solvent: benzyl benzoate; capsules not according to the invention; magnification lens: 10×

EXAMPLES

Figure 1:
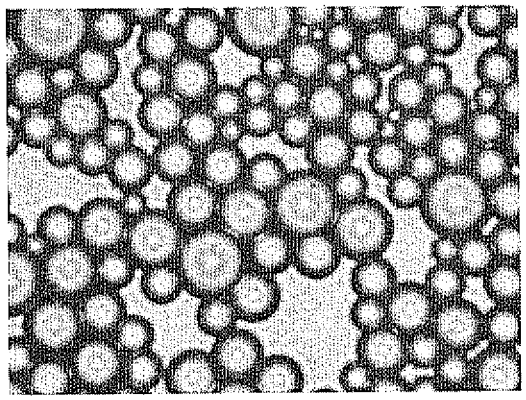
FIGS. 1 to 6 show the result of a test for the stability of microcapsules after drying-up by means of microscopic assessment according to the following Example 12. Specifically, the following capsules are shown.

Unless otherwise indicated, all particulars and data, in particular specified percentages and amounts, relate to weight.

Example 1

Production of a 3-aminopropyltriethoxysilane Hydrolysate 3-aminopropyltriethoxysilane (50 g), demineralized water (105 g) and sulfuric acid (97%, 2.35 g) were mixed and the alcohol resulting from the condensation was removed by distillation at normal pressure (40 g, mixed with small amounts of azeotropic water).

The solution obtained of the resulting polyaminosiloxane was approx. 20% in the solids content and was used without further modifications as the crosslinking agent for encapsulation tests.

Example 2

Encapsulation of Benzyl Benzoate in Capsules Made of Desmodur N 3300/3-aminopropyltriethoxysilane Hydrolysate, Diameter d=0.2-0.44 mm

| Substance used | Supplier | Amount |
| --- | --- | --- |
| Demineralized water | — | 122 g |
| Polyvinyl alcohol 18-88 (polyvinyl alcohol 16-20 mPa · s (4% in H$_2$O, 20° C.), degree of hydrolysis 86.7-88.7 mol %, residual acetylation 10.0-11.6%, DP ~2,700) | Fluka | 1.20 g |
| Benzyl benzoate | Symrise | 120 g |
| D&C Red No. 17 | Symrise | 0.03 g |
| Desmodur N3300 | Bayer Material Science | 4.00 g, 1.00 eq |
| 3-aminopropyltriethoxysilane hydrolysate from Example 1 | — | 11.1 g, approx. 1.03 eq |

To produce a continuous aqueous (homogeneous) phase, demineralized water (100 g) was placed in a beaker glass (1 l), polyvinyl alcohol 18-88 was stirred in and heated to 80° C. The mixture was left to cool to room temperature.

To produce the oil phase, the dye D&C Red No. 17 and Desmodur N3300 (4.00 g) were dissolved in benzyl benzoate (120 g). The oil phase was stirred into the homogeneous phase rapidly by means of a propeller stirrer at 400 rpm. A thermometer served as the flow breaker. The mixture was emulsified over 3 min at 400 rpm and a temperature of 23° C.

For the purposes of crosslinking, the 3-aminopropyltriethoxysilane hydrolysate from Example 1 (11.1 g), diluted with water (22.0 g), was added to the emulsion over a period of 10 min.

At 300 rpm, the temperature was increased over 30 min to 80° C. and the mixture was subsequently stirred at 80° C. for a further 2 hours.

A capsule dispersion was obtained, the capsules of which had a mean diameter of from 0.2-0.4 mm. N.B.: There was no observable free oil.

Example 3 (not According to the Invention)

Encapsulation of Benzyl Benzoate in Capsules Made of Desmodur N 3300/Guanidine Carbonate, Diameter d=0.2-0.44 mm

| Substance used | Supplier | Amount |
| --- | --- | --- |
| Demineralized water | — | 122 g |
| Polyvinyl alcohol 18-88 (polyvinyl alcohol 16-20 mPa · s (4% in H$_2$O, 20° C.), degree of hydrolysis 86.7-88.7 mol %, residual acetylation 10.0-11.6%, DP ~2,700) | Fluka | 1.20 g |
| Benzyl benzoate | Symrise | 120 g |
| D&C Blue No. 17 | Symrise | 0.03 g |
| Desmodur N3300 | Bayer Material Science | 4.00 g, 1.00 eq |
| Guanidine carbonate | Aldrich | 1.00 g, 1.07 eq |

To produce a continuous aqueous (homogeneous) phase, demineralized water (100 g) was placed in a beaker glass (1 l), polyvinyl alcohol 18-88 (1.20 g) was stirred in and heated to 80° C. The mixture was left to cool to room temperature.

To produce the oil phase, the dye D&C Blue No. 17 (0.03 g) and Desmodur N3300 (4.00 g) were dissolved in benzyl benzoate (120 g). The oil phase was stirred into the homogeneous phase rapidly by means of a propeller stirrer at 400 revolutions/min. A thermometer served as the flow breaker. The mixture was emulsified over 3 min at 400 rpm and a temperature of 23° C.

For the purposes of crosslinking, guanidine carbonate (1.00 g), dissolved in water (22.0 g), was added to the emulsion over a period of 10 min.

At 300 rpm, the temperature was increased over 30 min to 80° C. and the mixture was subsequently stirred at 80° C. for a further 2 hours.

A capsule dispersion was obtained, the capsules of which had a mean diameter of from 0.2-0.4 mm. N.B.: Low contents of free oil could be observed.

Example 4

Rapid Test for Assessing the Mechanical Stability of Capsules, Diameter d=0.2-0.4 mm A small sample is taken from a freshly produced capsule dispersion comprising capsules having a mean diameter of d=0.2-0.4 mm by means of a wide-neck pipette and pipetted onto a microscope slide in such a way that in a drop volume of approx. 0.75 ml a number of approx. 30 capsules come to lie on the microscope slide.

The microscope slide, with the drops resting thereon, is deposited horizontally on a white sheet of paper.

A second microscope slide is placed onto the microscope slide and drops by lateral positioning and slow lowering by tilting into the horizontal. The second microscope slide is positioned in such a way that (apart from the weight of the microscope slide) as little further force as possible acts on the sample.

It is observed whether individual, a plurality of or all capsules in the drop release their oil core.

By iterative, careful application of further microscope slides, it is determined from roughly what application force first capsules break open. An average microscope slide weighs in this case 4.6 g.

| Capsules according to Example 2 (according to the invention) | Capsules according to Example 4 (not according to the invention) |
| --- | --- |
| First capsules break on application of the 4$^{th}$ microscope slide, most of the capsules break on application of the 5$^{th}$ microscope slide | Most of the capsules break on application of the 1$^{st}$ microscope slide |

Example 5

Analytical Test Mixture for Encapsulation in the Follow-Up Examples

| Compound | % by mass, (based on the total mass of the mixture) |
| --- | --- |
| HEXANOL CIS-3 (cis-3-hexen-1-ol)- | 1.5 |
| ISOAMYL ACETATE | 1.5 |
| MANZANATE (ethyl 2-methylpentanoate) | 1.5 |
| PINEN ALPHA LAEVO NAT. (2-pinene) | 1.5 |
| PINEN BETA NAT. (2(10)-pinene) | 1.5 |
| LIMONENE D PURE (1,8-p-menthadiene) | 3.0 |
| TERPINENE GAMMA | 1.5 |
| DIHYDROMYRCENOL | 3.0 |

-continued

| Compound | % by mass, (based on the total mass of the mixture) |
|---|---|
| LINALOOL | 4.0 |
| BENZYL ACETATE | 3.0 |
| NEONONYL ACETATE | 3.0 |
| PHENYLACETALDEHYDE DIMETHYL ACETAL | 3.0 |
| CITRONELLOL 950 (3,7-dimethyl-6-octen-1-ol) | 3.0 |
| GERANIOL SUPRA (3,7-dimethyl-trans-2,6-octadien-1-ol) | 3.0 |
| LINALYL ACETATE | 4.5 |
| ISOBORNYL ACETATE | 4.5 |
| ALDEHYDE C11 (undecanal) | 3.0 |
| VANILLIN | 3.0 |
| HERBAFLORAT (4,7-methano-3a,4,5,6,7,7a-hexahydro-5 (or 6)-indenyl acetate) | 4.5 |
| IONONE, ALPHA | 4.5 |
| ISOEUGENOL | 4.5 |
| DECALACTONE, GAMMA | 4.5 |
| IRALDEIN, GAMM COEUR (3-methyl-4-(2.6.6-trimethylcyclohex-2-en-1-yl)but-3-en-2-one) | 4.5 |
| LILIAL | 6.0 |
| HELIONAL | 6.0 |
| ALDEHYDE C14 SOG. (γ-undecalactone) | 4.5 |
| HEDIONE | 6.0 |
| ALLYL IONONE | 3.0 |
| BENZYL BENZOATE | 3.0 |

Example 6

Encapsulation of a Solution of a Test Mixture in Isopropyl Myristate in Microcapsules Wall Material Made of Desmodur N3300, Substoichiometric Amount of Hydrosil 1151

| Substance used | Supplier | Amount |
|---|---|---|
| Demineralized water | — | 234 g |
| Polyvinyl alcohol 18-88 (polyvinyl alcohol 16-20 mPa · s (4% in H$_2$O, 20° C.), degree of hydrolysis 86.7-88.7 mol %, residual acetylation 10.0-11.6%, DP ~2,700) | Fluka | 2.40 g |
| Isopropyl myristate | Symrise | 191 g |
| Analytical test mixture from Example 5 | — | 50.0 g |
| D&C Red No. 17 | Symrise | 0.05 g |
| Desmodur N3300 | Bayer Material Science | 9.00 g |
| Dynasylan Hydrosil 1151 | Evonik Degussa Silanes | 6.85 g |

To produce a continuous aqueous (homogeneous) phase, demineralized water (200 g) was placed in a beaker glass (1 l), polyvinyl alcohol 18-88 (2.40 g) was stirred in and heated to 80° C. The mixture was left to cool to room temperature.

To produce the oil phase, a dye (in this case D&C Red No. 17, 0.05 g), an odorous substance mixture (in this case the analytical test mixture according to Example 5; 50 g) and a polyisocyanate (in this case Desmodur N3300, 9.00 g, approx. 46.7 mmol of NCO, approx. 1.00 eq) were dissolved in a solvent (in this case isopropyl myristate, 191 g). The oil phase was stirred into the homogeneous phase rapidly by means of a propeller stirrer at 400 revolutions/min. In a continuous operation, this preemulsion was further dispersed using an Ultra Turrax T50 basic and a flow chamber DK 50.11 at 5,200 revolutions/min for 10 min. The temperature of the emulsion was 21° C.

A crosslinking agent (in this case Dynaslan Hydrosil 1151, 6.85 g, 12.4 mmol of amine, approx. 0.27 eq), diluted with water (in this case 6.85 g), was added over a period of 60 sec while stirring using a propeller stirrer at 700 rpm.

The temperature was increased first over 10 min to 27° C., then within one hour to 80° C. with continued stirring. The mixture was subsequently stirred for a further 2 hours at 80° C.

A capsule dispersion was obtained, which is if appropriate cleaned, optionally by decanting and washing with water.

Example 7 (not According to the Invention)

Encapsulation of a Solution of a Test Mixture in Isopropyl Myristate in Microcapsules Wall material made of Desmodur N3300, substoichiometric amount of guanidine carbonate

| Substance used | Supplier | Amount |
|---|---|---|
| Demineralized water | — | 225 g |
| Polyvinyl alcohol 18-88 (polyvinyl alcohol 16-20 mPa · s (4% in H$_2$O, 20° C.), degree of hydrolysis 86.7-88.7 mol %, residual acetylation 10.0-11.6%, DP ~2,700) | Fluka | 2.40 g |
| Isopropyl myristate | Symrise | 191 g |
| Analytical test mixture from Example 5 | — | 50.0 g |
| D&C Turquoise No. 5 | Symrise | 0.05 g |
| Desmodur N3300 | Bayer Material Science | 9.00 g |
| Guanidine carbonate | Aldrich | 0.45 g |

A capsule dispersion comprising the foregoing substances used was produced in accordance with the description from Example 6. (Desmodur N3300: 9.00 g, approx. 46.7 mmol of NCO, approx. 1.00 eq; guanidine carbonate: 0.45 g, 9.99 mmol of amine, approx. 0.21 eq).

The mean particle diameter was 10.1 µm, determined by light-scattering experiments in a Mastersizer.

Example 8

Encapsulation of a Solution of a Test Mixture in Benzyl Benzoate in Microcapsules Wall material made of Desmodur XP2410, substoichiometric amount of Hydrosil 1151

| Substance used | Supplier | Amount |
|---|---|---|
| Demineralized water | — | 234 g |
| Polyvinyl alcohol 18-88 (polyvinyl alcohol 16-20 mPa · s (4% in H$_2$O, 20° C.), degree of hydrolysis 86.7-88.7 mol %, residual acetylation 10.0-11.6%, DP ~2,700) | Fluka | 2.40 g |
| Benzyl benzoate | Symrise | 176 g |
| Analytical test mixture from Example 5 | — | 50.0 g |
| D&C Red No. 17 | Symrise | 0.05 g |
| Desmodur XP 2410 | Bayer Material Science | 16.0 g |
| Hydrosil 1151 | Evonik Degussa Silanes | 12.16 g |

A capsule dispersion comprising the foregoing substances used was produced in accordance with the description from Example 6. (Desmodur XP 2410: 16.00 g, approx. 90.6 mmol of NCO, approx. 1.00 eq; Hydrosil 1151: 12.16 g, approx. 22.0 mmol of amine, approx. 0.24 eq).

Example 9 (not According to the Invention)

Encapsulation of a Solution of a Test Mixture in Benzyl Benzoate in Microcapsules Wall material made of Desmodur XP2410, substoichiometric amount of guanidine carbonate

| Substance used | Supplier | Amount |
| --- | --- | --- |
| Demineralized water | — | 224 g |
| Polyvinyl alcohol 18-88 (polyvinyl alcohol 16-20 mPa · s (4% in $H_2O$, 20° C.), degree of hydrolysis 86.7-88.7 mol %, residual acetylation 10.0-11.6%, DP ~2,700) | Fluka | 2.40 g |
| Benzyl benzoate | Symrise | 176 g |
| Analytical test mixture from Example 5 | — | 50.0 g |
| D&C Turquoise No. 5 | Symrise | 0.05 g |
| Desmodur XP 2410 | Bayer Material Science | 16.0 g |
| Guanidine carbonate | Aldrich | 0.80 g |

A capsule dispersion comprising the foregoing substances used was produced in accordance with the description from Example 6. (Desmodur XP 2410: 16.00 g, approx. 90.6 mmol of NCO, approx. 1.00 eq; guanidine carbonate: 0.80 g, 17.8 mmol of amine, approx. 0.20 eq).

Example 10

Encapsulation of a Solution of a Test Mixture in Benzyl Benzoate in Microcapsules Wall material made of Desmodur N3300, substoichiometric amount of Hydrosil 1151

| Substance used | Supplier | Amount |
| --- | --- | --- |
| Demineralized water | — | 224 g |
| Polyvinyl alcohol 18-88 (polyvinyl alcohol 16-20 mPa · s (4% in $H_2O$, 20° C.), degree of hydrolysis 86.7-88.7 mol %, residual acetylation 10.0-11.6%, DP ~2,700) | Fluka | 2.40 g |
| Benzyl benzoate | Symrise | 191 g |
| Analytical test mixture from Example 5 | — | 50.0 g |
| D&C Turquoise No. 5 | Symrise | 0.05 g |
| Desmodur N3300 | Bayer Material Science | 9.00 g |
| Hydrosil 1151 | Evonik Degussa Silanes | 6.85 g |

A capsule dispersion comprising the foregoing substances used was produced in accordance with the description from Example 6. (Desmodur N3300: 9.00 g, approx. 46.7 mmol of NCO, approx. 1.00 eq; Hydrosil 1151: 6.85 g, approx. 12.4 mmol of amine, approx. 0.27 eq).

Example 11 (not According to the Invention)

Encapsulation of a Solution of a Test Mixture In Benzyl Benzoate in Microcapsules Wall material made of Desmodur XP2410, substoichiometric amount of guanidine carbonate

| Substance used | Supplier | Amount |
| --- | --- | --- |
| Demineralized water | — | 224 g |
| Polyvinyl alcohol 18-88 (polyvinyl alcohol 16-20 mPa · s (4% in $H_2O$, 20° C.), degree of hydrolysis 86.7-88.7 mol %, residual acetylation 10.0-11.6%, DP ~2,700) | Fluka | 2.40 g |
| Benzyl benzoate | Symrise | 191 g |
| Analytical test mixture from Example 5 | — | 50.0 g |
| D&C Turquoise No. 5 | Symrise | 0.05 g |
| Desmodur N3300 | Bayer Material Science | 9.00 g |
| Guanidine carbonate | Aldrich | 0.45 g |

A capsule dispersion comprising the foregoing substances used was produced in accordance with the description from Example 6. (Desmodur N3300: 9.00 g, approx. 46.7 mmol of NCO, approx. 1.00 eq; guanidine carbonate: 0.45 g, approx. 9.99 mmol of amine, approx. 0.21 eq).

Example 12

Laboratory Rapid Test for the Stability of Microcapsules by Drying-Up and Microscopic Assessment For assessing the stability of microcapsules during drying-up, 1 ml of capsule dispersion (if appropriate diluted with water in a ratio of 10/1) was in each case applied to a microscope slide. The drop was spread out spread out carefully using a wide spatula. The drop was allowed to dry up for 20 min at room temperature. The sample was assessed under a microscope.

Microscope: Binocular Axiostar plus from Zeiss with phototube and Canon PowerShot A640 camera.

Unless otherwise indicated, the following recording conditions were selected:

Microscope: lens 100×, Hellfeld

Camera: 640×480, no image compression, digital zoom 1.4×

Figure 2:
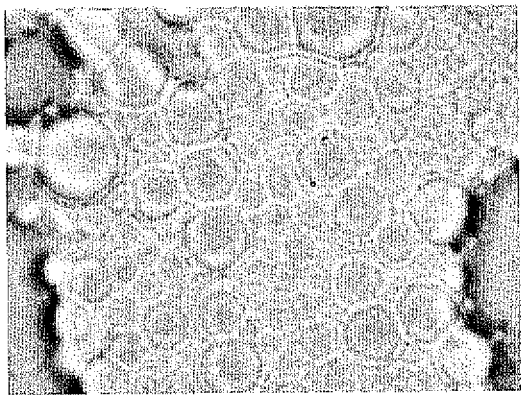
Figure 3:
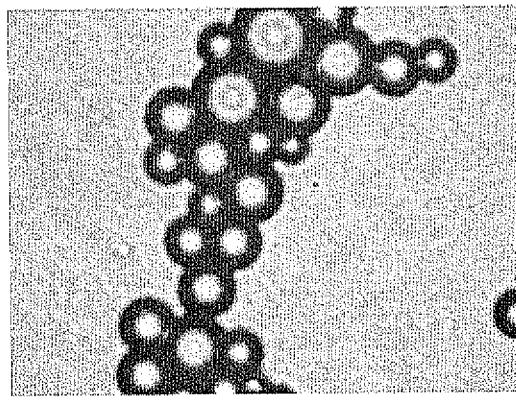
Figure 4:
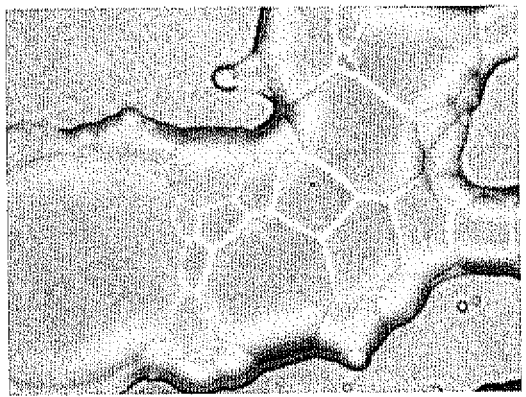
Figure 5:
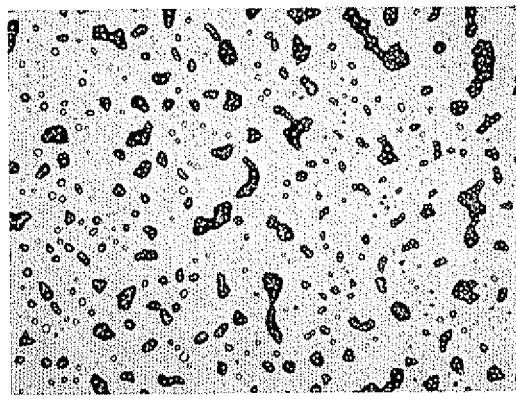
Figure 6:
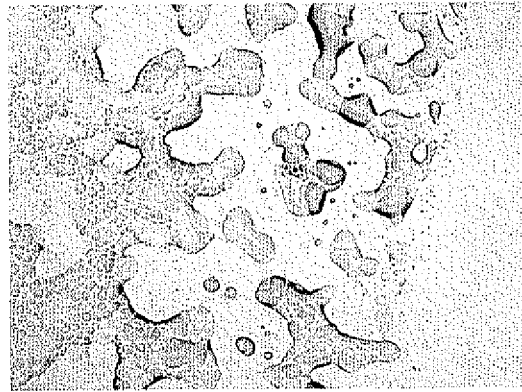

Results of the capsule dispersions examined in the rapid test:

| | Crosslinking agent: Hydrosil 1151 (according to the invention) | Crosslinking agent: Guanidine carbonate (not according to the invention) |
| --- | --- | --- |
| Polyisocyanate: Desmodur N3300 Solvent: Isopropyl myristate | Capsules from Example 6: stable (FIG. 1) | Capsules from Example 7: unstable (FIG. 2) |
| Polyisocyanate: Desmodur XP2410 Solvent: Benzyl benzoate | Capsules from Example 8: stable (FIG. 3) | Capsules from Example 9: unstable (FIG. 4) |
| Polyisocyanate: Desmodur N3300 Solvent: Benzyl benzoate | Capsules from Example 10: stable (FIG. 5) | Capsules from Example 11: unstable (FIG. 6) |

Example 13

Encapsulation of an Individual Odorous Substance in Microcapsules Made of Hydrosil 1151 and Desmodur N3300

| Substance used | Supplier | Amount |
| --- | --- | --- |
| Demineralized water | — | 435 g |
| Polyvinyl alcohol 18-88 (polyvinyl alcohol 16-20 mPa · s (4% in H₂O, 20° C.), degree of hydrolysis 86.7-88.7 mol %, residual acetylation 10.0-11.6%, DP ~2,700) | Fluka | 5.10 g |
| Manzanate (ethyl 2-methylpentanoate) | Givaudan | 125.0 g |
| D&C Turquoise No. 6 | Symrise | 0.03 g |
| Desmodur N3300 | Bayer Material Science | 9.00 g |
| Dynasylan Hydrosil 1151 | Evonik Degussa Silanes | 34.6 g |

To produce a continuous, aqueous (homogeneous) phase, demineralized water (425 g) was placed in a beaker glass (1 l), polyvinyl alcohol 18-88 (5.1 g) was stirred in and heated to 80° C. The mixture was left to cool to room temperature.

To produce the oil phase, a dye (in this case D&C Turquoise No. 6, 0.03 g) and a polyisocyanate (in this case Desmodur N3300, 9.00 g) were dissolved in an odorous substance (in this case manzanate, 125 g). The oil phase was stirred into the homogeneous phase rapidly by means of a propeller stirrer at 400 revolutions/min. In a continuous operation, this preemulsion was further dispersed using an Ultra Turrax T50 basic and a flow chamber DK 50.11 at 4,800 rpm for 5 min. The temperature of the emulsion was 26° C.

A crosslinking agent (in this case Dynaslan Hydrosil 1151, 34.6 g), diluted with water (in this case 10.0 g), was added over a period of 30 sec while stirring using a propeller stirrer at 500 rpm.

The temperature was first left for 2 hours at 22° C. with continued stirring. The temperature was then increased over 2 hours to 40° C. and the mixture was subsequently stirred for a further 2 hours at 40° C.

A capsule dispersion was obtained, in which the microcapsules are deposited within 6 hours as the lighter phase.

The mean capsule diameter determined in the microscope was 9.5 μm.

The capsule system was incorporated into a typical fabric softener formulation (Example 15).

Microscopic examinations of the fabric softener samples reveal that the capsule system was stable in the fabric softener formulation.

Example 14 (not According to the Invention)

Encapsulation of an Individual Odorous Substance ("Manzanate", ethyl 2-methylpentanoate) in Microcapsules Made of Guanidine and Desmodur N3300

| Substance used | Supplier | Amount |
| --- | --- | --- |
| Demineralized water | — | 468 g |
| Polyvinyl alcohol 18-88 (polyvinyl alcohol 16-20 mPa · s (4% in H₂O, 20° C.), degree of hydrolysis 86.7-88.7 mol %, residual acetylation 10.0-11.6%, DP ~2,700) | Fluka | 5.10 g |
| Manzanate (ethyl 2-methylpentanoate) | Givaudan | 125.0 g |
| D&C Turquoise No. 6 | Symrise | 0.03 g |
| Desmodur N3300 | Bayer Material Science | 9.00 g |
| Guanidine carbonate | Aldrich | 2.27 g |

A capsule dispersion comprising the foregoing substances used was produced in accordance with the description from Example 13.

The mean capsule diameter determined in the microscope was 8.6 μm.

The capsule system was incorporated into a typical fabric softener formulation (Example 15). Microscopic examinations of the fabric softener samples reveal that the capsule system was stable in the fabric softener formulation.

Example 15 (not According to the Invention)

Fabric Softener Formulation

| Substance used | Chemical name | Supplier | % by weight |
| --- | --- | --- | --- |
| Water, deionized | Water | — | 94.10 |
| Mergal K9N | 5-chloro-2-methyl-3(2H)-isothiazolone and 2-methyl-3-(2H)-isothiazolone | Troy Chemie, Seelze | 0.10 |
| Dow Corning 1520 Antifoam | Dow Corning GmbH, Germany | Polydimethylsiloxane | 0.30 |
| Rewoquat WE18 | Evonic Goldschmidt GmbH | Dialkylester ammonium methosulfate | 5.50 |

The invention claimed is:

1. A capsule comprising a core and a shell surrounding the core,
wherein the shell comprises a polymeric material, and wherein the polymeric material is produced by reacting a component (A) with a component (B), wherein component (A) comprises one or more polysiloxanes bearing one or more amino groups and component (B) comprises one or more polyisocyanates; and the polymeric material comprises groups of structure G1:

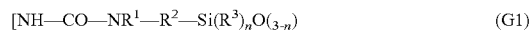

$$[NH\text{—}CO\text{—}NR^1\text{—}R^2\text{—}Si(R^3)_nO_{(3-n)}] \quad (G1)$$

and optionally comprises groups of structure G2:

$$[NH\text{—}CO\text{—}NH] \quad (G2)$$

wherein:
R¹ is selected from the group consisting of H, an NH₂-substituted unbranched alkyl, an NH₂-substituted branched alkyl and an NH₂-substituted cycloalkyl;
R² is an unsaturated or saturated hydrocarbon;
R³ is selected from the group consisting of unbranched or branched alkyl and cycloalkyl;
n=0 or 1; and
each O atom bound directly to the Si atom of G1 is bound directly to a further Si atom.

2. The capsule as claimed in claim 1, wherein the reaction is an interfacial reaction comprising contacting a first phase comprising component (A) with a second phase comprising component (B).

3. The capsule as claimed in claim 2, wherein the second phase is dispersed in the first phase during the interfacial reaction and wherein the second phase further comprises one or more further ingredients of the core.

4. The capsule as claimed in claim 3, wherein the further ingredient or ingredients are chemically inert with respect to component (B).

5. The capsule as claimed in claim 3, wherein the second phase is emulsified in the first phase during the interfacial reaction.

6. The capsule as claimed in claim 1, wherein (i) the amino group-bearing polysiloxanes of component (A) are water-soluble and/or (ii) the polyisocyanates of component (B) are water-insoluble.

7. The capsule as claimed in claim 1, wherein (i) the amino group-bearing polysiloxanes of component (A) are present in the form of an aqueous solution or an aqueous colloid and/or (ii) the polyisocyanates of component (B) are present in the form of a dispersion in water during the reaction.

8. The capsule as claimed in claim 1, wherein the amino group-bearing polysiloxanes of component (A) are produced by a process comprising:
(i) providing or producing:
(a) one or more aminoalkylalkoxysilanes of formula (I)

and
(b) optionally providing or producing one or more further silanes of formula (II)

wherein:
$R^1$ is selected from the group consisting of H, an $NH_2$-substituted unbranched alkyl, an $NH_2$-substituted branched alkyl and an $NH_2$-substituted cycloalkyl,
$R^2$ is an unbranched or branched alkylene,
$R^4$ is selected from the group consisting of unbranched or branched alkyl and cycloalkyl,
each $X^1$ is, independently of each further $X^1$, a hydrolyzable group,
each $R^5$ is, independently of each further $R^5$, selected from the group consisting of unbranched or branched alkyl and cycloalkyl,
each $X^2$ is, independently of each further $X^2$, a hydrolyzable group,
x=0 or 1,
y=0, 1 or 2,
(ii) producing an aqueous solution of the aforementioned compounds,
(iii) setting process conditions to ensure the hydrolyzable groups are hydrolyzed,
(iv) removing compounds $HX^1$ and $HX^2$ from the mixture.

9. The capsule as claimed in claim 8, wherein:
$R^1$ is selected from the group consisting of H, an $NH_2$-substituted unbranched alkyl, an $NH_2$-substituted branched alkyl containing 1 to 8 C atoms, and cycloalkyl containing 3 to 6 C atoms,
$R^2$ is an unbranched or branched alkylene containing 1 to 8 C atoms,
$R^4$ is selected from the group consisting of unbranched or branched alkyl containing 1 to 8 C atoms and cycloalkyl containing 3 to 6 C atoms,
each $X^1$ is, independently of each further $X^1$, an alkyloxy containing 1 to 4 C atoms,
each $R^5$ is, independently of each further $R^5$, selected from the group consisting of unbranched or branched alkyl containing 1 to 8 C atoms and cycloalkyl containing 3 to 6 C atoms,
and/or
each $X^2$ is, independently of each further $X^2$, an alkyloxy containing 1 to 4 C atoms.

10. The capsule as claimed in claim 1, wherein, component (A) comprises 0.2 to 4 mol of amino groups per 1 mol of isocyanate groups present in component (B).

11. The capsule as claimed in claim 1, wherein the polyisocyanate or polyisocyanates of component (B) comprise two or more isocyanate groups per molecule.

12. The capsule as claimed in claim 11, wherein the polyisocyanate or polyisocyanates of component (B) are selected from the group consisting of hexamethylene diisocyanate, isophorone diisocyanate and derivatives thereof, wherein each of the derivatives comprises two or more isocyanate groups and further comprises one or more groups selected from the group consisting of biuret, isocyanurate, uretdione and iminooxadiazinedione.

13. The capsule as claimed in claim 1, wherein the capsule has a diameter of 1 to 500 µm.

14. The capsule as claimed in claim 1, wherein the core comprises one or more further ingredients selected from the group consisting of odorous substance, dye, dye precursor, catalyst for chemical reactions, adhesive, reactive substance for adhesive applications, pharmaceutical active substance, cosmetic active substance, plant protection active substance, water repellent, flame retardant and solvent.

15. The capsule as claimed in claim 1, wherein the core comprises one or more odorous substances selected from the group consisting of
extracts of natural raw materials and also fractions thereof, or ingredients isolated therefrom;
individual odorous substances from a group of hydrocarbons;
aliphatic aldehydes and acetals thereof;
aliphatic ketones and oximes thereof;
aliphatic sulfur-containing compounds;
aliphatic nitriles;
esters of aliphatic carboxylic acids;
formates, acetates, propionates, isobutyrates, butyrates, isovalerates, pentanoates, hexanoates, crotonates, tiglinates and 3-methyl-2-butenoates of acyclic terpene alcohols;
acyclic terpene aldehydes and ketones and also dimethyl and diethyl acetals thereof;
cyclic terpene aldehydes and ketones;
cyclic and cycloaliphatic ethers;
cyclic and macrocyclic ketones;
cycloaliphatic aldehydes;
cycloaliphatic ketones;
esters of cyclic alcohols;
esters of cycloaliphatic alcohols;
esters of cycloaliphatic carboxylic acids;
esters of araliphatic alcohols and aliphatic carboxylic acids;
araliphatic ethers;
aromatic and araliphatic aldehydes;
aromatic and araliphatic ketones;
aromatic and araliphatic carboxylic acids and esters thereof;
nitrogen-containing aromatic compounds;
phenyl ethers and phenyl esters;

heterocyclic compounds; and
lactones,
wherein the shell is completely or substantially impervious to the odorous substance or substances.

16. A product comprising a capsule as claimed in claim 1.

17. The product as claimed in claim 16, wherein the product is a consumer goods product selected from the group consisting of personal care product, home care product and laundry care product.

18. A perfumed product comprising a capsule as claimed in claim 1.

19. A process for producing a capsule as claimed in claim 1, comprising:
  (i) providing one or more substances to be encapsulated, one or more polyisocyanates and optionally providing a solvent,
  (ii) providing or producing polysiloxanes bearing one or more amino groups,
  (iii) producing a solution (1) comprising the substance or substances to be encapsulated, the polyisocyanate or polyisocyanates and the solvent, if present, wherein the solution (1) is not soluble in water,
  (iv) producing a dispersion of solution (1) in an aqueous solution or an aqueous colloid of the polysiloxane or polysiloxanes,
  (v) reacting the polyisocyanate or polyisocyanates with the polysiloxane or polysiloxanes, and
  (vi) optionally subsequently maintaining the temperature in a range of 40 to 80° C. for 0.5 to 5 hours.

* * * * *